US010047458B2

(12) United States Patent
Bernt et al.

(10) Patent No.: US 10,047,458 B2
(45) Date of Patent: Aug. 14, 2018

(54) REGENERATED CELLULOSE FIBER

(71) Applicant: KELHEIM FIBRES GMBH, Kelheim (DE)

(72) Inventors: Ingo Bernt, Regensburg (DE); Walter Roggenstein, Bad Abbach (DE); Calvin Woodings, Earthrope (GB); Haio Harms, Gmunden (AT)

(73) Assignee: Kelheim Fibres GmbH, Kelheim (DE)

( * ) Notice: Subject to any disclaimer, the term of this patent is extended or adjusted under 35 U.S.C. 154(b) by 0 days.

(21) Appl. No.: 14/828,835

(22) Filed: Aug. 18, 2015

(65) Prior Publication Data

US 2015/0354095 A1 Dec. 10, 2015

Related U.S. Application Data

(63) Continuation of application No. 13/387,277, filed as application No. PCT/EP2010/059870 on Jul. 9, 2010, now Pat. No. 9,279,196.

(30) Foreign Application Priority Data

Jul. 31, 2009 (EP) .................................... 09450139

(51) Int. Cl.
*A61F 13/15* (2006.01)
*D01D 5/247* (2006.01)
(Continued)

(52) U.S. Cl.
CPC .............. *D01D 5/247* (2013.01); *A61L 15/28* (2013.01); *D01F 2/06* (2013.01); *A61F 13/2051* (2013.01);
(Continued)

(58) Field of Classification Search
CPC .......... A61F 13/53; A61F 2013/530007; A61F 2013/530036; A61F 2013/530043; A61F 2013/530051
(Continued)

(56) References Cited

U.S. PATENT DOCUMENTS 2,476,293 A 7/1949 Hall et al.
2,913,769 A * 11/1959 Kastli .................. D06M 11/155
106/122
(Continued)

FOREIGN PATENT DOCUMENTS

AU 757461 B2 2/2003
EP 1 091 770 A1 4/2001
(Continued)

OTHER PUBLICATIONS

C.R. Woodings et al., "The Manufacture, Properties and Uses of Inflated Viscose Fibers," Lenzinge Berichte, vol. 58, Jan. 1, 1985, pp. 33-39 (XP02562009).
(Continued)

*Primary Examiner* — Jacqueline Stephens
(74) *Attorney, Agent, or Firm* — Fitzpatrick, Cella, Harper & Scinto

(57) ABSTRACT

The present invention relates to a regenerated cellulose fiber, which is characterized by the combination of the following features:
  the fiber has in its dry condition a collapsed hollow cross-sectional structure
  the fiber has in its wet condition a cross-sectional structure with cavities
  the fiber is segmented in the longitudinal direction by dividing walls
  there is incorporated into the fiber an absorbent polymer, in particular carboxymethylcellulose.
(Continued)

The fiber may be obtained by a process, wherein there is admixed a carbonate as well as an absorbent polymer, in particular carboxymethylcellulose, to a viscose dope.

15 Claims, 2 Drawing Sheets

(51) Int. Cl.
*A61L 15/28* (2006.01)
*D01F 2/06* (2006.01)
*A61F 13/20* (2006.01)
*D01D 5/24* (2006.01)
*D01D 5/253* (2006.01)

(52) U.S. Cl.
CPC ............... *A61F 2013/15365* (2013.01); *A61F 2013/15447* (2013.01); *A61F 2013/15463* (2013.01); *D01D 5/24* (2013.01); *D01D 5/253* (2013.01); *D10B 2201/24* (2013.01); *D10B 2509/02* (2013.01); *D10B 2509/026* (2013.01); *Y10T 428/2904* (2015.01); *Y10T 428/2975* (2015.01)

(58) Field of Classification Search
USPC ........ 604/378, 374, 375, 376, 384, 367, 366
See application file for complete search history.

(56) References Cited

U.S. PATENT DOCUMENTS

| | | | |
|---|---|---|---|
| 3,318,990 A | 5/1967 | Kajitani | |
| 3,699,965 A | 10/1972 | Dostal | |
| 4,182,735 A | 1/1980 | Costa, Jr. et al. | |
| 4,199,367 A * | 4/1980 | Smith | A61L 15/225 106/162.8 |
| 4,289,824 A | 9/1981 | Smith | |
| 4,399,255 A | 8/1983 | Smith et al. | |
| 5,124,197 A * | 6/1992 | Bernardin | A61L 15/28 428/393 |
| 6,548,730 B1 | 4/2003 | Patel et al. | |

FOREIGN PATENT DOCUMENTS

| | | |
|---|---|---|
| GB | 758 651 A | 10/1956 |
| GB | 1 086 496 A | 10/1967 |
| GB | 1 333 047 A | 10/1973 |
| GB | 1 393 778 A | 5/1975 |
| JP | 53143722 A | 12/1978 |
| WO | 00/01425 A1 | 1/2000 |

OTHER PUBLICATIONS

English Translation of International Preliminary Report on Patentability issued in the International Application No. PCT/EP2010/059870.

C.R. Woodings, et al., "The Manufacture, Properties and Uses of Inflated Viscose Fibres", Lenzinger Berichte, Jun. 1985, pp. 33-39.

* cited by examiner

REGENERATED CELLULOSE FIBER

The present application is a continuation of U.S. patent application Ser. No. 13/387,277, filed Jan. 26, 2012, which is a national stage filing under 35 U.S.C. § 371 of International Patent Application No. PCT/EP2010/059870, filed Jul. 9, 2010, which claims priority to European Patent Application No. EP09450139.2, filed Jul. 31, 2009, the entire disclosure of each of which is incorporated by reference herein.

BACKGROUND OF THE INVENTION

Field of the Invention

The present invention relates to a regenerated cellulose fiber prepared by the viscose process.

In particular the invention relates to a regenerated cellulose fiber with a collapsed hollow cross-sectional structure.

For sanitary uses such as, for example, tampons or absorbent cores in general, fibers are desirable, which have an especially high water storing capacity in order to in this way allow for a possibly high absorption capacity of the sanitary product.

Conventional super-absorbent materials have the disadvantage that they usually form a gel upon contact with water and thus reduce the integrity of the absorbent core and, furthermore, block the further transport of liquid through the absorbent core. The integrity of the absorbent core, hence, is important in these applications, as there is prevented, by means of this material, the exit of the absorption material and thus the contamination of, for example, wounds.

It is also desired for wound dressings that the absorbing material does not agglutinate with the wound so that it is achievable to remove the dressing from the wound without causing pain.

Another demand for the fiber material in these fields of application is the flawless processability in conventional production techniques for the fleece production.

Viscose fibers with a high portion of carboxymethylcellulose (CMC) have been known. This is a mixed fiber that is obtained by spinning in carboxymethylcellulose into the viscose dope. Such fibers have also been commercially produced (U.S. Pat. Nos. 4,199,367 A, 4,289,824 A).

The production of viscose fibers with a hollow cross-sectional structure ("hollow fibers") by spinning in sodium carbonate into the viscose dope has already been known since 1920. Fibers of this type were previously commercially produced by various producers. Hollow fibers of the "superinflated" type with high water retention capacity have been produced especially for sanitary applications (GB 1,333,047 A, GB 1,393,778 A).

A comprehensive survey on development and history of hollow viscose fibers may be found with: C. R. Woodings, A. J. Bartholomew; "The manufacture properties and uses of inflated viscose rayon fibers"; TAPPI Nonwovens Symposium; 1985; pp. 155-165.

Viscose-CMC mixed fibers show in their production the disadvantage that due to their high absorbance and the strong adherence of the fibers to each other in a wet condition (gel effect on the fiber surface) the fibers in the conventional viscose process, from an integration of about 15% CMC based on the cellulose on, tend to sink in the baths of the subsequent treatment and not to float like conventional viscose fibers. This substantially hinders the production of these fibers in a common commercial process.

A desired effect of these fibers is their gel-like surface consistency in a wet condition. This effect in touch, however, is partly reduced by the fact that these fibers have an extremely grooved surface structure—like conventional viscose fibers.

The maximum increase of the water retention capacity of such fibers is restricted, as during the spinning in of >50% CMC there arise great problems in the processing step thereof.

Also with hollow viscose fibers the increase of the water retention capacity is limited. Due to a stronger inflation of the fiber, there will not be obtained any higher water retention capacity anymore from a certain level on, and there are rather formed band-like fibers with a flat cross-section having low water retention capacity, wherein the post-treatment thereof in a staple fiber method is rather associated with problems due to their large and smooth surface and the high fiber-fiber binding capacity associated therewith.

There are further known carboxymethylated fibers, i.e. fibers that have been produced by subsequent carboxymethylation of viscose fibers (commercially available as "Aquacell" fibers of the company Convatec; U.S. Pat. No. 6,548,730 B1; AU 757461 B; WO00/01425 A1; EP 1 091 770 A1). The fibers allow for a high amount of water absorption but form upon contact with water a gel with simultaneous complete loss of the fiber structure, which is not desirable for all possible applications.

The U.S. Pat. No. 3,318,990 describes a method for the production of flat viscose fibers, wherein there is admixed to the viscose, on the one side, sodium carbonate and, on the other side, a high-molecular substance swelling in water, e.g., CMC.

The resulting fibers are described as completely flat. The collapsed cross-sectional structure retains its form also in a wet condition. The fibers are suitable for the production of paper according to U.S. Pat. No. 3,318,990.

SUMMARY OF THE INVENTION

The present invention has the objective to provide a viscose fiber with a possibly high water retention capacity, a possibly high absorption under pressure and an additional surface gel effect. The fiber is to be produced in the conventional methods for the production of viscose fibers and to be processed according to the conventional method for the production of fleece (for example, carding, solidification by needling, hydro-entanglement, thermal solidification, calandration).

This task is solved by a regenerated cellulose fiber which is characterized by the combination of the following features:
 the fiber has in its dry condition a collapsed hollow cross-sectional structure
 the fiber has in its wet condition a cross-sectional structure with cavities
 the fiber is segmented in the longitudinal direction by dividing walls
 there is incorporated into the fiber an absorbent polymer.
The cellulose fibers are produced by
 providing a viscose dope
 admixing a carbonate compatible with viscose into the viscose dope
 admixing an absorbent polymer into the viscose dope
 spinning the viscose dope in a spinning bath, thereby forming fibers, wherein the degree of ripening of the viscose dope before spinning is less than 15° Hottenroth, preferably 10° to 14° Hottenroth, the content of $H_2SO_4$ in the spinning bath is 8% to 10% the content of $ZnSO_4$ in the spinning bath is 0.3% to 0.5% and the content of $Na_2SO_4$ in the spinning bath is 25% to 30%.

DETAILED DESCRIPTION OF THE INVENTION

Figure 1:
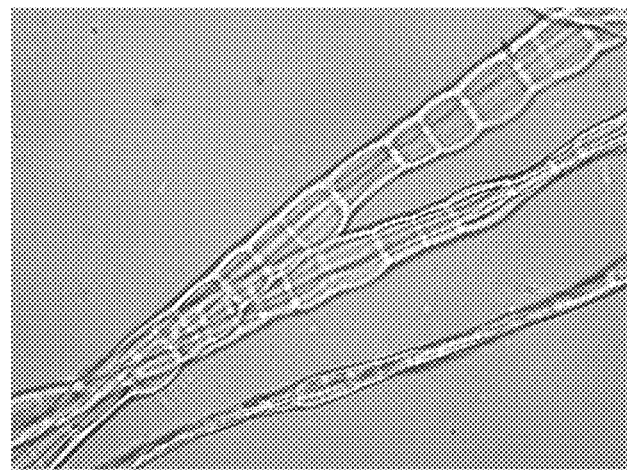
FIG. 1 shows the longitudinal section of a dried cellulose fiber according to the invention.

The present invention provides a regenerated cellulose fiber with a collapsed hollow cross-sectional structure, which is characterized by the combination of the following features:

the fiber has in its dry condition a collapsed hollow cross-sectional structure the fiber has in its wet condition a cross-sectional structure with cavities the fiber is segmented in the longitudinal direction by dividing walls there is incorporated into the fiber an absorbent polymer.

The absorbent polymer is preferably carboxymethylcellulose (CMC). Other suitable absorbent polymers may be selected from the group of polymers that are compatible with the viscose process, such as, for example, viscose carbamate, carboxymethylcellulose, alginates or homo- and co-polymers of acrylic acids (such as, for example, described in U.S. Pat. No. 4,399,255).

By means of the present invention, there is, for the very first time, provided in the preferred embodiment a combination of a hollow viscose fiber, which has a tubular structure with cavities again upon re-wetting, and a viscose mixed fiber with CMC.

The expert understands that a regenerated cellulose fiber with collapsed hollow cross-sectional structure is a viscose fiber, the cross-section of which has been so strongly inflated that the cross-sectional structure collapses in itself. The production of such fibers (through admixture of sodium carbonate) is described in GB 1,333,047 A and GB 1,393,778 A.

The fiber according to the invention has in its dried condition preferably an irregular multilobal cross-section or an irregularly grooved cross-section. Such fibers are also designated as "SI" fibers (for superinflated). In contrast to the fibers described in the U.S. Pat. No. 3,318,990 A the cross-section will re-open upon wetting of the fibers and it will regain its tubular form, with cavities being formed.

The fiber according to the invention is different to the fibers described in U.S. Pat. No. 3,318,990 A in particular due to the presence of a segmentation in the longitudinal direction as a result of dividing walls.

The distance between the dividing walls thus is preferably between 0.3 and 3 times, preferably 0.5 to 2 times, the fiber width averaged over the fiber length. There is assumed that the presence of these dividing walls is in part responsible for the fact that upon wetting of the fibers, there is re-formed a tubular structure with cavities.

This tubular structure is probably responsible for the fibers according to the invention having excellent absorbance compared to the fibers of the U.S. Pat. No. 3,318,990 that remain flat also upon re-wetting.

By the measure that there is incorporated an absorbent polymer, in particular CMC; into the fiber the expert understands as being integrated, in the matrix of the (upon regeneration of the fiber) underivatized cellulose, the absorbent polymer, for example CMC. This is—in contrast to the application of CMC onto the already fabricated fiber—possible, especially, by spinning in CMC into the viscose dope.

The cellulose fiber according to the invention has a very high water retention capacity; the fiber character, however, still remains the same in its wet condition. Furthermore, there has been shown that the fiber according to the invention, in contrast to conventional viscose-CMS mixed fibers, may be well produced and in particular processed in a conventional viscose process.

The portion of absorbent polymer, in particular of CMC, in the fiber according to the invention is preferably 5 to 50% by weight, especially preferably 15 to 40% by weight, most preferably 20 to 30% by weight, based upon the underivatized cellulose.

The cellulose fiber according to the invention is preferably available in the form of a staple fibers and may be produced in all common titer areas. Preferably, the fiber titer may be 0.5 dtex to 8 dtex, preferably from 1.3 to 6 dtex.

The fiber length of the fiber according to the invention may be from 2 mm to 80 mm and is dependent in particular on the field of application. For a wet-laid process, there are suitable in particular fiber lengths of 2 to 20 mm, for a carding process, fiber lengths from 20 to 80 mm are suitable.

The tenacity of the fiber according to the invention is typically above 10 cN/tex; the tear elongation is above 15%.

The cellulose fiber according to the invention has preferably a water retention capacity of at least 300%, measured according to DIN 53814.

There was, for example, measured in the fibers according to the invention with a portion of 35% by weight CMC a water retention capacity of up to 400% WRC.

A cylindrical tampon prepared from the fiber according to the invention with a mass of 2.72 g, a length of 44 mm and a diameter of 13 mm has preferably a Syngina value of at least 5.2 g/g, measured according to EDANA/INDA Standard Test Methods for the Nonwovens and Related Industries ERT 350.0 or WSP 350.1, respectively.

In this way, the fiber has a higher Syngina value than the currently commercially most important absorbent viscose fiber, a viscose fiber with a regular trilobal cross-section marketed under the trade name "Galaxy"® (EP 0 301 874 A1).

For the production of a regenerated cellulose fiber according to the present invention, there is used a process, comprising the steps providing a viscose dope admixing a carbonate compatible with viscose into the viscose dope admixing of an absorbent polymer into the viscose dope spinning the viscose dope in a spinning bath, thereby forming fibers, wherein the degree of ripening of the viscose dope before spinning is less than 15° Hottenroth, preferably 10° to 14° Hottenroth the content of $H_2SO_4$ in the spinning bath is 8% to 10% the content of ZnSO$_4$ in the spinning bath is 0.3% to 0.5% and the content of Na$_2$SO$_4$ in the spinning bath is 25% to 30%.

The process according to the invention, hence, combines the so far known step of spinning in a carbonate, in particular sodium carbonate, for producing a hollow cross-section, with the step of spinning in an absorbent polymer.

In comparison with the method described in U.S. Pat. No. 3,318,990, there is spun in the process according to the invention a viscose with a lower degree of ripening (expressed in Hottenroth) and the spinning bath has a smaller portion of H$_2$SO$_4$ and ZnSO$_4$. There is made the assumption that these different procedures result in the differences mentioned above between the fiber according to the invention and the fiber described in the U.S. Pat. No. 3,318,990, in particular in terms of cross-sectional structure and also in terms of the other characteristics.

The absorbent polymer is preferably CMC. The following embodiments relate to this preferred embodiment; they apply, however, mutatis mutandis also to other absorbent polymers that are compatible with the viscose process.

As carbonate, there is suitable any carbonate, in particular an alkali metal carbonate, which is compatible with the conditions of the viscose process. Especially suitable is sodium carbonate. Other suitable carbonates are potassium carbonate, calcium carbonate as well as in general all carbonates releasing carbon dioxide under the influence of an acid.

Exerting influence on the cross-sectional form of the fiber (inflation and collapse) in a way so that there is developed a collapsed hollow cross-sectional structure, for example, by selecting the appropriate conditions in the spinning bath, selection of temperature and, of course, amount of carbonate added, is known to the expert in particular from the patent publications cited above.

Preferably, the carbonate is admixed in an amount of 11% by weight to 23% by weight (calculated as $(CO_3)^2$), based on the cellulose in the viscose dope. In the specific case of sodium carbonate, the preferred amount is from 20% by weight to 40% by weight based on cellulose.

Further preferably, the absorbent polymer, in particular the carboxymethylcellulose, is admixed in an amount of 5% by weight to 50% by weight, especially preferably 15% by weight to 40% by weight, most preferably 20% by weight to 30% by weight, based on the cellulose in the viscose dope.

The carbonate and/or the carboxymethylcellulose may preferably be admixed in the form of a solution.

In particular, the carboxymethylcellulose may be admixed in the form of an alkaline solution, containing 2% by weight to 9% by weight, preferably 3% by weight to 5% by weight NaOH and 5% by weight to 15% by weight, preferably 6% by weight to 12% by weight, carboxymethylcellulose.

The carbonate and the carboxymethylcellulose may also be admixed together, in particular in the form of a joint solution.

For the production of a cellulose fiber according to the invention there may also be used a conventional viscose dope.

A typical embodiment of the process according to the invention comprises the following measures:

To a viscose dope produced according to conventional methods (cellulose content=9-10%, NaOH content 5-6%; viscosity 30-50 falling ball seconds, degree of ripening 10-15° Hottenroth) there are added 25-35% by weight Na$_2$CO$_3$ (to be varied according to fiber titer), based on the cellulose in the viscose dope, in the form of a 20% solution of Na$_2$CO$_3$. There are further added to the dope 5% by weight to 45% by weight, preferably 20% by weight to 30% by weight, based on the cellulose in the viscose dope, carboxymethylcellulose in the form of an alkaline solution (2-9% by weight NaOH; preferably 3-5% by weight). The concentration of the solution is 5% by weight to 15% by weight, preferably 8-12% by weight. The carboxymethylcellulose is a commercially available product with a degree of substitution DS of 0.6-1.2, preferably 0.65-0.85 and a viscosity (2% solution; 25° C.) of 30-800 mPas; preferably 50-100 mPas.

The additive solutions (carbonate and CMC) are preferably injected into the already spinnable viscose dope, in particular immediately before the spinning. The viscose is subsequently homogenized, preferably via a dynamic mixer.

The viscose is spun out and subjected to a post-treatment at parameters common for textile fibers.

EXAMPLES

For the production of regenerated cellulose fibers described in the following there was used a conventional viscose dope.

Experiment A: spinning of the viscose dope without additives

Experiment B: spinning of the viscose dope with 30% Na$_2$CO$_3$ based on cellulose Experiment C (according to the invention): spinning of the viscose dope with 30% Na$_2$CO$_3$ and 20% CMC (DS=0.81; viscosity 2%=53 mPas, Type Blanose 7M1F, producer: company Aqualon France (Hercules)), each based on the cellulose present in the viscose dope.

The dopes were spun out into fibers with a titer of 4.4 dtex with identical spinning parameters.

Experiment D: spinning of the viscose dope without additives

Experiment E: spinning of the viscose dope with 20% CMC (specification as in experiment C) based on cellulose Experiment F: spinning of the viscose dope with 30% CMC (specification as in experiment C) based on cellulose The dopes were spun out into fibers with a titer of 3 dtex with identical spinning parameters.

Morphology of the Produced Fibers

Viewed with a microscope, the fibers B and C are hollow fibers of the SI type (superinflated, segmented). The fibers A, D, E and F are fibers with a grooved and round cross-section that is typical for viscose fibers.

Figure 2:
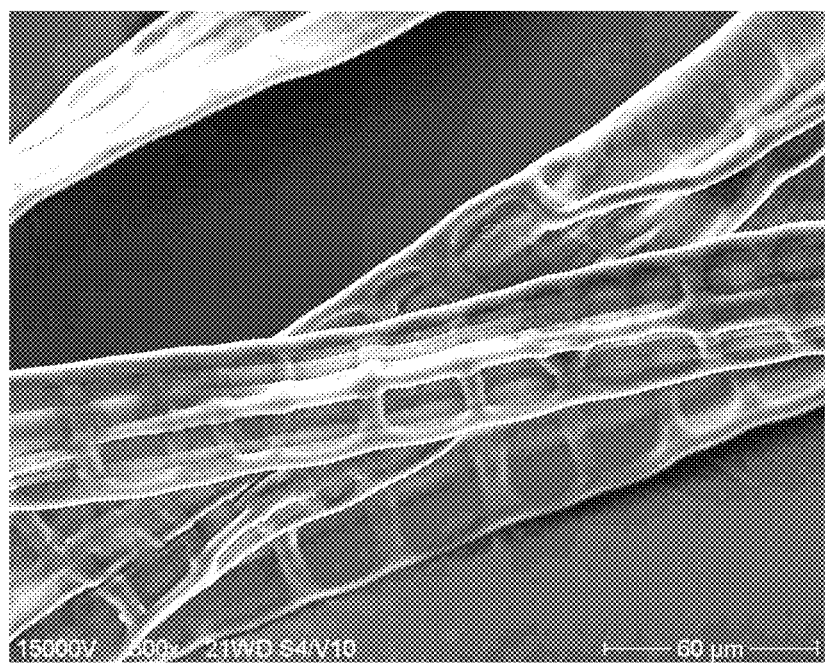
FIG. 2 shows a much enlarged longitudinal section of a dried cellulose fiber according to the invention.
Figure 3:
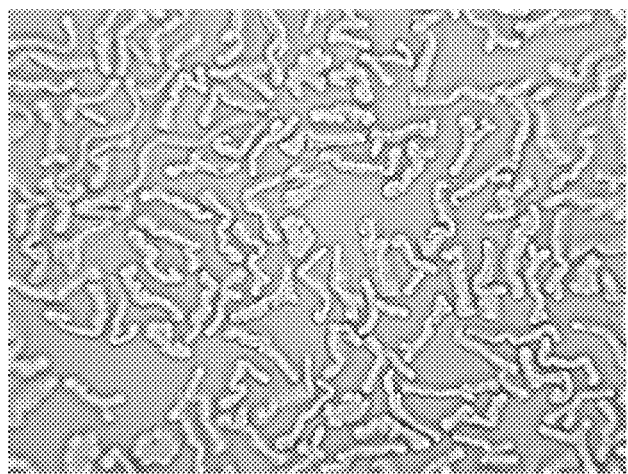
FIG. 3 shows the cross-section of dried cellulose fibers according to the invention.

Longitudinal section and cross section of the dried fiber C according to the invention are illustrated in the FIGS. 1, 2 and 3.

In the FIGS. 1 and 2 there is clearly visible the segmentation in the longitudinal direction, which is typical for the fiber according to the invention. The segmentation is the result of dividing walls, which—as may be recognized in FIG. 2 in an increased magnification—in fact result in a rigid and membrane-like sub-division.

In FIG. 3 there is visible the collapsed hollow cross-sectional structure, which is typical for "SI" fibers, with the formation of a plurality of sides or irregularly grooved cross-sections.

Figure 4:
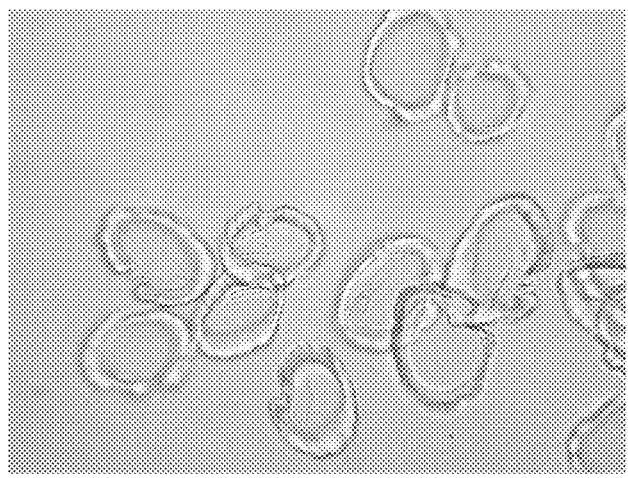
FIG. 4 shows the tubular cross-section of a cellulose fiber according to the invention upon contact with water.

FIG. 4 shows the tubular cross-section of the fiber according to the invention upon wetting of the dry fiber.

Spinning Performance:

All fibers may be spun with the conventional parameters. Whereas the fibers E and F tend to deposit in the baths of the post-treatment of the fibers, this effect is not observable in the fiber C according to the invention.

Water Retention Capacity:

For all fibers, the water retention capacity was measured in % according to DIN 53814.

Fiber A: 80%
Fiber B: 220%
Fiber C: 335%
Fiber D: 93%
Fiber E: 149%
Fiber F: 193%

As the results show, the water retention capacity in absolute terms may be increased by spinning in 20% CMC based on the cellulose by about 50%, by spinning in 30% CMC by 100%. (comparison of the fibers D->E->F).

By spinning in 30% $Na_2CO_3$ based on cellulose, the water retention capacity may be increased by 140%. (comparison of the percentage, fiber A->B).

By spinning in 20% CMC and 30% $Na_2CO_3$ based on cellulose (according to the invention), the water retention capacity, however, may be increased by 255%. This shows that the effects of the two additives do no increase additively but rather synergistically:

The effect of the addition of CMC alone or $Na_2CO_3$ alone, respectively, amounts to:

A->B=+140%
D->E=+56%

The expected value for the fiber C, hence, would be 80+140+56=276%

As the measured water retention capacity of the fiber amounting to 335% is higher by the factor 1.2, the two additive components surprisingly, hence, act in a synergistic way.

Gel Effect:

The surface gel effect (slimy and soapy touch) is somehow stronger in the fibers C according to the invention than in the comparative sample E (with the same content of CMC). This gel effect is only developed in a wet condition.

Fiber Values:

The fiber C according to the invention obtains at a titer of 4.4 dtex a tenacitiy of 13.1 cN/tex with a tension of 22.9%, which is acceptable for a use in the field of fleece processing.

Absorption Under Pressure:

From the fibers A, B and C there were pressed tampon plugs, each amounting to 2.72 g, and there was carried out an Syngina measurement according to WSP 351.0. As an additional reference, there was produced an identically produced plug made of 100% commercial trilobal viscose fiber ("Galaxy"®).

Results:

Fiber A: 4.56 g/g
Fiber B: 4.75 g/g
Fiber C: 5.73 g/g
100% Galaxy: 5.05 g/g

The result shows that with the fibers according to the invention there may be obtained a significantly higher Syngina absorption even in comparison with commercial trilobal fibers.

The regenerated cellulose fiber according to the invention, hence, is especially suitable for the use in absorbing products, sanitary products, in particular tampons, sanitary aids for incontinence, sanitary napkins and panty liners, packaging of foodstuff, in particular for meat products, papers, in particular filter papers, clothes (e.g., clothing textiles for the moisture management in combination with other fibers or as multi-layered construction) and wound dressings.

The invention claimed is:

1. A regenerated cellulose fiber, wherein:
   the fiber is a superinflated fiber
   the fiber is segmented in the longitudinal direction by dividing walls
   the fiber further comprises an absorbent polymer.
2. The cellulose fiber according to claim 1, wherein the fiber has a cross-section in the dry condition that is multi-lobal and/or is irregularly grooved.
3. The cellulose fiber according to claim 1 or 2, wherein the fiber has a width and a length, wherein the fiber comprises dividing walls and wherein the distance between the dividing walls is between 0.3 and 3 times the fiber width averaged over the fiber length.
4. The cellulose fiber according to claim 3, the distance between the dividing walls is between 0.5 and 2 times the fiber width averaged over the fiber length.
5. The cellulose fiber according to claim 1 or 2, wherein the fiber comprises-5% by weight to 50% by weight of the absorbent polymer based on underivatized cellulose.
6. The cellulose fiber according to claim 5, wherein the fiber comprises 15% by weight to 40% by weight of the absorbent polymer based on underivatized cellulose.
7. The cellulose fiber according to claim 5, wherein the fiber comprises 20% by weight to 30% by weight of the absorbent polymer based on underivatized cellulose.
8. The cellulose fiber according to claim 1 or 2, wherein the absorbent polymer is carboxymethylcellulose.
9. The cellulose fiber according to claim 1 or 2, wherein said cellulose fiber is present in the form of a staple fiber.
10. The cellulose fiber according to claim 1 or 2, wherein the fiber has a titer of 0.5 dtex to 8 dtex.
11. The cellulose fiber according to claim 10, wherein the fiber has a titer of 1.3 dtex to 6 dtex.
12. The cellulose fiber according to claim 1 or 2, wherein the fiber has a length which is from 2 mm to 80 mm.
13. The cellulose fiber according to claim 1 or 2, characterized by a water retention capacity of at least 300%.
14. A cylindrical tampon obtained from the cellulose fiber according to claim 1 or 2, wherein said cylindrical tampon has a mass of 2.72 g, a length of 44 mm, a diameter of 13 mm and a Syngina value of at least 5.2 g/g.
15. The regenerated cellulose fiber according to claim 1 or 2 for use in absorbing products, sanitary products, in particular tampons, sanitary aids for incontinence, sanitary napkins and panty liners, packaging of foodstuff, in particular for meat products, papers, in particular filter papers, clothes and wound dressings.

* * * * *